United States Patent [19]

Lehrer et al.

[11] Patent Number: 5,464,823

[45] Date of Patent: Nov. 7, 1995

[54] MAMMALIAN ANTIBIOTIC PEPTIDES

[75] Inventors: Robert I. Lehrer, Santa Monica; Vladimir N. Kokryakov, Los Angeles; Sylvia S. L. Harwig, Woodland Hills, all of Calif.

[73] Assignee: The Regents of the University of California, Oakland, Calif.

[21] Appl. No.: 95,769

[22] Filed: Jul. 26, 1993

Related U.S. Application Data

[63] Continuation-in-part of Ser. No. 93,926, Jul. 20, 1993.

[51] Int. Cl.$^6$ .............................. C07K 7/00; A61K 38/10
[52] U.S. Cl. .............................. 514/13; 514/12; 530/324; 530/325; 530/326
[58] Field of Search ................................... 530/326, 325, 530/324; 514/13, 12; 536/23.5; 435/69.1

[56] References Cited

U.S. PATENT DOCUMENTS

| | | | |
|---|---|---|---|
| 4,543,252 | 9/1985 | Lehrer et al. | 514/12 |
| 4,659,692 | 4/1987 | Lehrer et al. | 514/12 |
| 4,705,777 | 11/1987 | Lehrer et al. | 514/12 |

OTHER PUBLICATIONS

Kokryakar et al., Jul. 26, 1993, FEBS 327(2):231–236.
Robsen et al. 1986. Introduction to Protein Engineering, Elsevier, New York, p. 41.
Pongor, 1987, Methods in Enzymology 154:450–473.
Nakamura et al., Tachyplesin, a Class of Antimicorbial Peptide from the Hemocytes of the Horseshoe Crab (*Tachypleus tridentatus*), J. Biol. Chem. (1988) 263:16709–16713.
Miyata et al., Antimicrobial Peptides, Isolated from Horseshoe Crab Hemocytes, Tachyplesin II, and Polyphemusins I and II: Chemical Structures and Biological Activity, J. Biochem; (1989) 106:663–668.
Murakami et al., Direct Virus Inactivation of Tachyplesin I and Its Isopeptides from Horseshoe Crab Hemocytes, Chemotherapy (1991) 37:327–334.

Morimoto et al., Inhibitory Effect of Tachyplesin I on the Proliferation of Human Immunodeficiency Virus in vitro, Chemotherapy (1991) 37:206–211.
Nakashima et al., Anti–Human Immunodeficiency Virus Activity of a Novel Synthetic Peptide, T22 ([Tyr–5,12, Lys–7]Polyphemusin II): a Possible Inhibitor of Virus–Cell Fusion, Antimicrobial Agents and Chemotherapy (1992) 1249–1255.
Lehrer et al., Defensins: Endogenous Antibiotic Peptides of Animal Cells, Cell (1991) 64:229–230.
Lehrer et al., Defensins: Antimicrobial and Cytotoxic Peptides of Mammalian Cells, Annual Review Immunol (1993) 11:105–128.
Selsted et al., Purification, Primary Structures, and Antibacterial Activities of β–Defensins, a New Family of Antimicrobial Peptides from Bovine Neutrophils, J. Biol Chem (1993) 288:6641–6648.
Diamond et al., Tracheal antimicrobial peptide, a cysteine–rich peptide from mammalian tracheal mucosa: Peptide isolation and cloning of a cDNA, Proc. Natl. Acad. Sci. (USA) (1991) 88:3952–3958.

(List continued on next page.)

*Primary Examiner*—Keith C. Furman
*Attorney, Agent, or Firm*—Morrison & Foerster

[57] ABSTRACT

Peptide-based compounds containing four invariant cysteine residues which have been oxidized to obtain two intramolecular disulfide bonds are useful as preservatives and in preventing, treating, or ameliorating viral or microbial infection in animals and plants. These compounds, in one embodiment, are of the formula:

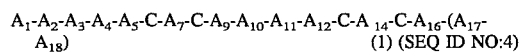

$$A_1\text{-}A_2\text{-}A_3\text{-}A_4\text{-}A_5\text{-}C\text{-}A_7\text{-}C\text{-}A_9\text{-}A_{10}\text{-}A_{11}\text{-}A_{12}\text{-}C\text{-}A_{14}\text{-}C\text{-}A_{16}\text{-}(A_{17}\text{-}A_{18}) \quad (1)\ (\text{SEQ ID NO:4})$$

and the N-terminal acylated, C-terminal amidated or esterified and the cystine-bridged forms thereof
wherein $A_1$, $A_9$, $A_{10}$ and $A_{11}$ are basic amino acids;
$A_2$ and $A_3$ are small amino acids;
$A_5$, $A_7$, $A_{12}$, $A_{14}$ and $A_{16}$ are hydrophobic amino acids; and
$A_4$ is a basic or a small amino acid;
$A_{17}$ is not present or, if present, is a small amino acid;
$A_{18}$ is not present or, if present, is a basic amino acid.

18 Claims, 5 Drawing Sheets

OTHER PUBLICATIONS

Lambert et al., Insect Immunity: Isolation from immune blood of the dipteran *Phormia terranovae* of two insect antibacterial peptides with sequence homology to rabbit lung macrophage bactericidal peptides, Proc. Natl. Acad. Sci. (USA) (1989) 88:262–265.

Broekaert et al., Antimicrobial Peptides from *Amaranthus caudatus* Seeds with Sequence Homology to the Cysteine/Clycine–Rich Domain o Chitin–Binding Proteins, Biochemistry (1992) 31:4308–4314.

Cornelissen et al., Strategies for Control of Fungal Disease with Transgenic Plants, Plant Physiol (1993) 101:709–712.

Haln et al., Disease resistance results from foreign phytoalexin expression in a novel plant, Nature (1993) 361:153–156.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:1:

```
Arg Gly Gly Arg Leu Cys Tyr Cys Arg Arg Arg Phe Cys Val Cys Val
1               5                   10                  15
Gly Arg
```

( 2 ) INFORMATION FOR SEQ ID NO:2:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( x i ) SEQUENCE DESCRIPTION: SEQ ID NO:2:

```
Arg Gly Gly Arg Leu Cys Tyr Cys Arg Arg Arg Phe Cys Ile Cys Val
1               5                   10                  15
```

( 2 ) INFORMATION FOR SEQ ID NO:3:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:3:

```
Arg Gly Gly Gly Leu Cys Tyr Cys Arg Arg Arg Phe Cys Val Cys Val
1               5                   10                  15
Gly Arg
```

( 2 ) INFORMATION FOR SEQ ID NO:4:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is A1 =basic amino acid."

( i x ) FEATURE:
        ( A ) NAME/KEY: Modified-site
        ( B ) LOCATION: 2
        ( D ) OTHER INFORMATION: /note="This position is A2 =small
                amino acid."

( i x ) FEATURE:
        ( A ) NAME/KEY: Modified-site
        ( B ) LOCATION: 3
        ( D ) OTHER INFORMATION: /note="This position is A3 =small
                amino acid."

( i x ) FEATURE:
        ( A ) NAME/KEY: Modified-site
        ( B ) LOCATION: 4
        ( D ) OTHER INFORMATION: /note="This position is A4 =basic
                or small amino acid."

( i x ) FEATURE:
        ( A ) NAME/KEY: Modified-site
        ( B ) LOCATION: 5
        ( D ) OTHER INFORMATION: /note="This position is A5 =
                hydrophobic amino acid."

( i x ) FEATURE:
        ( A ) NAME/KEY: Modified-site
        ( B ) LOCATION: 7
        ( D ) OTHER INFORMATION: /note="This position is A7 =
                hydrophobic amino acid."

( i x ) FEATURE:
        ( A ) NAME/KEY: Modified-site
        ( B ) LOCATION: 9
        ( D ) OTHER INFORMATION: /note="This position is A9 =basic
                amino acid."

( i x ) FEATURE:
        ( A ) NAME/KEY: Modified-site
        ( B ) LOCATION: 10
        ( D ) OTHER INFORMATION: /note="This position is A10 =
                basic amino acid."

( i x ) FEATURE:
        ( A ) NAME/KEY: Modified-site
        ( B ) LOCATION: 11
        ( D ) OTHER INFORMATION: /note="This position is A11 =
                basic amino acid."

( i x ) FEATURE:
        ( A ) NAME/KEY: Modified-site
        ( B ) LOCATION: 12
        ( D ) OTHER INFORMATION: /note="This position is A12 =
                hydrophobic amino acid."

( i x ) FEATURE:
        ( A ) NAME/KEY: Modified-site
        ( B ) LOCATION: 14
        ( D ) OTHER INFORMATION: /note="This position is A14 =
                hydrophobic amino acid."

( i x ) FEATURE:
        ( A ) NAME/KEY: Modified-site
        ( B ) LOCATION: 16
        ( D ) OTHER INFORMATION: /note="This position is A16 =
                hydrophobic amino acid."

( i x ) FEATURE:
        ( A ) NAME/KEY: Modified-site
        ( B ) LOCATION: 17
        ( D ) OTHER INFORMATION: /note="This position is A17 =not
                present or, if present, a small amino a..."

( i x ) FEATURE:
        ( A ) NAME/KEY: Modified-site
        ( B ) LOCATION: 18
        ( D ) OTHER INFORMATION: /note="This position is A18 =not
                present or, if present, a basic amino a..."

( x i ) SEQUENCE DESCRIPTION: SEQ ID NO:4:

Xaa Xaa Xaa Xaa Xaa Cys Xaa Cys Xaa Xaa Xaa Xaa Cys Xaa Cys Xaa
1               5                       10                      15

Xaa Xaa ( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is A19 =an amino acid residue."

( i x ) FEATURE:
        ( A ) NAME/KEY: Modified-site
        ( B ) LOCATION: 2
        ( D ) OTHER INFORMATION: /note="This position is A20 =an amino acid residue."

( i x ) FEATURE:
        ( A ) NAME/KEY: Modified-site
        ( B ) LOCATION: 3
        ( D ) OTHER INFORMATION: /note="This position is A21 =an amino acid residue."

( i x ) FEATURE:
        ( A ) NAME/KEY: Modified-site
        ( B ) LOCATION: 4
        ( D ) OTHER INFORMATION: /note="This position is A22 =an amino acid residue."

( i x ) FEATURE:
        ( A ) NAME/KEY: Modified-site
        ( B ) LOCATION: 5
        ( D ) OTHER INFORMATION: /note="This position is A23 =an amino acid residue."

( i x ) FEATURE:
        ( A ) NAME/KEY: Modified-site
        ( B ) LOCATION: 7
        ( D ) OTHER INFORMATION: /note="This position is A24 =an amino acid residue."

( i x ) FEATURE:
        ( A ) NAME/KEY: Modified-site
        ( B ) LOCATION: 9
        ( D ) OTHER INFORMATION: /note="This position is A25 =an amino acid residue."

( i x ) FEATURE:
        ( A ) NAME/KEY: Modified-site
        ( B ) LOCATION: 10
        ( D ) OTHER INFORMATION: /note="This position is A26 =an amino acid residue."

( i x ) FEATURE:
        ( A ) NAME/KEY: Modified-site
        ( B ) LOCATION: 11
        ( D ) OTHER INFORMATION: /note="This position is A27 =an amino acid residue."

( i x ) FEATURE:
        ( A ) NAME/KEY: Modified-site
        ( B ) LOCATION: 12
        ( D ) OTHER INFORMATION: /note="This position is A28 =an amino acid residue."

( i x ) FEATURE:
        ( A ) NAME/KEY: Modified-site
        ( B ) LOCATION: 14

(D) OTHER INFORMATION: /note="This position is A29 =an amino acid residue."

(ix) FEATURE:
    (A) NAME/KEY: Modified-site
    (B) LOCATION: 16
    (D) OTHER INFORMATION: /note="This position is A30 =an amino acid residue."

(ix) FEATURE:
    (A) NAME/KEY: Modified-site
    (B) LOCATION: 17
    (D) OTHER INFORMATION: /note="This position is A31 =an amino acid residue."

(ix) FEATURE:
    (A) NAME/KEY: Modified-site
    (B) LOCATION: 18
    (D) OTHER INFORMATION: /note="This position is A32 =an amino acid residue."

(xi) SEQUENCE DESCRIPTION: SEQ ID NO:5:

Xaa Xaa Xaa Xaa Xaa Cys Xaa Cys Xaa Xaa Xaa Xaa Cys Xaa Cys Xaa
1               5                       10                  15

Xaa Xaa

MAMMALIAN ANTIBIOTIC PEPTIDES

This invention was made with funding from NIH Grant No. A122839. The U.S. Government has certain rights in this invention. This application is a continuation-in-part of U.S. Ser. No. 07/093,926 filed 20 Jul. 1993, the contents of which are incorporated herein by reference.

TECHNICAL FIELD

The invention relates to the field of antibiotic peptides. In particular, the invention concerns short peptides, some of which are isolated from porcine leukocytes, that have a wide range of antimicrobial activities.

BACKGROUND ART

One of the defense mechanisms against infection by both animals and plants is the production of peptides that have antimicrobial and antiviral activity. Various classes of these peptides have been isolated from tissues both of plants and animals. One, well known class of such peptides is the tachyplesins which were first isolated from the hemocytes of the horseshoe crab as described by Nakamura, T. et al. *J Biol Chem* (1988) 263:16709–16713. This article described the initial tachyplesin isolated from the Japanese species, Tachyplesin I, which is a 17-amino acid amidated peptide containing four cysteine residues providing two intramolecular cystine bonds. In a later article by this group, Miyata, T. et al. *J Biochem* (1989) 106:663–668, extends the studies to the American horseshoe crab and isolated a second tachyplesin, Tachyplesin II, consisting of 17 residues amidated at the C-terminus, also containing four cysteine residues and two intramolecular disulfide bonds. Two additional 18-mers, called polyphemusins, highly homologous to Tachyplesin II and containing the same positions for the four cysteine residues, were also isolated. Polyphemusin I and Polyphemusin II differ from each other only in the replacement of one arginine residue by a lysine. All of the peptides were described as having antifungal and antibacterial activity. A later article by Murakami, T. et al. *Chemotherapy* (1991) 37:327–334, describes the antiviral activity of the tachyplesins with respect to vesicular stomatus virus; Herpes Simplex Virus I & II, Adenovirus I, Reovirus II and Poliovirus I were resistant to inactivation by Tachyplesin I. Morimoto, M. et al. *Chemotherapy* (1991) 37:206–211, found that Tachyplesin I was inhibitory to Human Immunodeficiency Virus. This anti-HIV activity was found also to be possessed by a synthetic analog of Polyphemusin II as described by Nakashima, H. et al. *Antimicrobial Agents and Chemotherapy* (1992) 1249–1255.

Other important classes of cysteine-containing antimicrobial peptides include the defensins, β-defensins and insect defensins. The defensins are somewhat longer peptides characterized by six invariant cysteines and three intramolecular cystine disulfide bonds. Defensins were described by Lehrer, R. I. et al. *Cell* (1991) 64:229–230; Lehrer, R. I. et al. *Ann Rev Immunol* (1993) 11:105–128. A review of mammalian-derived defensins by Lehrer, R. I. et al. is found in *Annual Review Immunol* (1993) 11:105–128; three patents have issued on the defensins: U.S. Pat. Nos. 4,705,777; 4,659,692; and 4,543,252. Defensins have been found in the polymorphonucleated neutrophils (PMN) of humans and of several other animals, as well as in rabbit pulmonary alveolar macrophages, and in murine small intestinal epithelial (Paneth) cells and in corresponding cells in humans.

β-Defensins are found in bovine respiratory epithelial cells, bovine granulocytes and avian leukocytes. See Selsted, M. E. et al. *J Biol Chem* (1993) 288:6641–6648 and Diamond, G. et al. *Proc Natl Acad Sci* (USA) (1991) 88:3952–3958. Insect defensins have been reported by Lambert, J. et al. *Proc. Natl Acad Sci* (USA) (1989) 88:262–265.

Antifungal and antibacterial peptides and proteins have also been found in plants (Broekaert, W. F. et al. *Biochemistry* (1992) 31:4308–4314) as reviewed by Cornelissen, B. J. C. et al. *Plant Physiol* (1993) 101:709–712. Expression systems for the production of such peptides have been used to transform plants to protect the plants against such infection as described, for example, by Haln, R. et al. *Nature* (1993) 361:153–156.

The present invention provides a new class of antimicrobial and antiviral peptides, representative members of which have been isolated from porcine leukocytes. These peptides are useful as antibacterial antiviral and antifungal agents in both plants and animals.

DISCLOSURE OF THE INVENTION

The invention is directed to peptides of 16–18 amino acid residues characterized by four invariant cysteines and by a characteristic pattern of basic and hydrophobic amino acids and/or being isolatable from animal leukocytes using the method of the invention. These peptides can be produced synthetically or recombinantly, or can be isolated from their native sources and purified for use as preservatives or in pharmaceutical compositions in treating or preventing infection in animals. Alternatively, the peptides can be formulated into compositions which can be applied to plants to protect them against viral or microbial infection. In still another approach, the DNA encoding the peptides can be expressed in situ, in animals or preferably in plants, to combat infections.

Accordingly, in one aspect, the invention is directed to peptides of the formula:

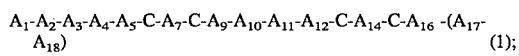

$$A_1\text{-}A_2\text{-}A_3\text{-}A_4\text{-}A_5\text{-}C\text{-}A_7\text{-}C\text{-}A_9\text{-}A_{10}\text{-}A_{11}\text{-}A_{12}\text{-}C\text{-}A_{14}\text{-}C\text{-}A_{16}\text{-}(A_{17}\text{-}A_{18}) \quad (1);$$

and the amidated and/or acylated, and/or cyclic forms thereof, wherein $A_1$, $A_9$, $A_{10}$ and $A_{11}$ are basic amino acids;

$A_2$ and $A_3$ are small amino acids;

$A_5$, $A_7$, $A_{12}$, $A_{14}$ and $A_{16}$ are hydrophobic amino acids;

$A_4$ is a basic or a small amino acid;

$A_{17}$ is either not present or is a small amino acid; and $A_{18}$ is not present if $A_{17}$ is not present or, if $A_{17}$ is present, $A_{18}$ may be not present or is a basic amino acid.

In another aspect, the invention comprises a peptide of the formula:

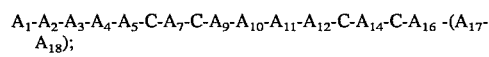

$$A_1\text{-}A_2\text{-}A_3\text{-}A_4\text{-}A_5\text{-}C\text{-}A_7\text{-}C\text{-}A_9\text{-}A_{10}\text{-}A_{11}\text{-}A_{12}\text{-}C\text{-}A_{14}\text{-}C\text{-}A_{16}\text{-}(A_{17}\text{-}A_{18});$$

and the amidated and/or acylated and/or cyclic forms thereof wherein $A_{1-5}$, $A_7$, $A_{9-12}$ and $A_{14}$ and $A_{16}$, and, if present, $A_{17}$ and $A_{18}$ (i.e. $A_n$), represent amino acid residues which peptides are isolatable from animal leukocytes by the methods similar to those described herein.

In still other aspects, the invention is directed to recombinant materials useful for the production of the peptides of the invention as well as plants or animals modified to contain expression systems for the production of these peptides. The invention is also directed to pharmaceutical compositions and compositions for application to plants containing the peptides of the invention as active ingredients or compositions which contain expression systems for production of the peptides or for in situ expression of the nucleotide sequence encoding these peptides. The invention is also directed to methods to prepare the invention peptides synthetically, to antibodies specific for these peptides, and to the use of the peptides as preservatives.

BRIEF DESCRIPTION OF THE DRAWINGS

FIG. 4a shows antibacterial activity against *E. Coli*;

FIG. 4b shows antibacterial activity against *Listeria monocytogenes*;

FIG. 4c shows antifungal activity against *Candida albicans*;

FIG. 5a shows activity against *Candida albicans* in 100 µM Nacl;

FIG. 5b shows activity against *E. Coli* in 100 µM Nacl;

FIG. 5c shows activity against *Candida albicans* in 90% fetal calf serum.

MODES OF CARRYING OUT THE INVENTION

Figure 1:
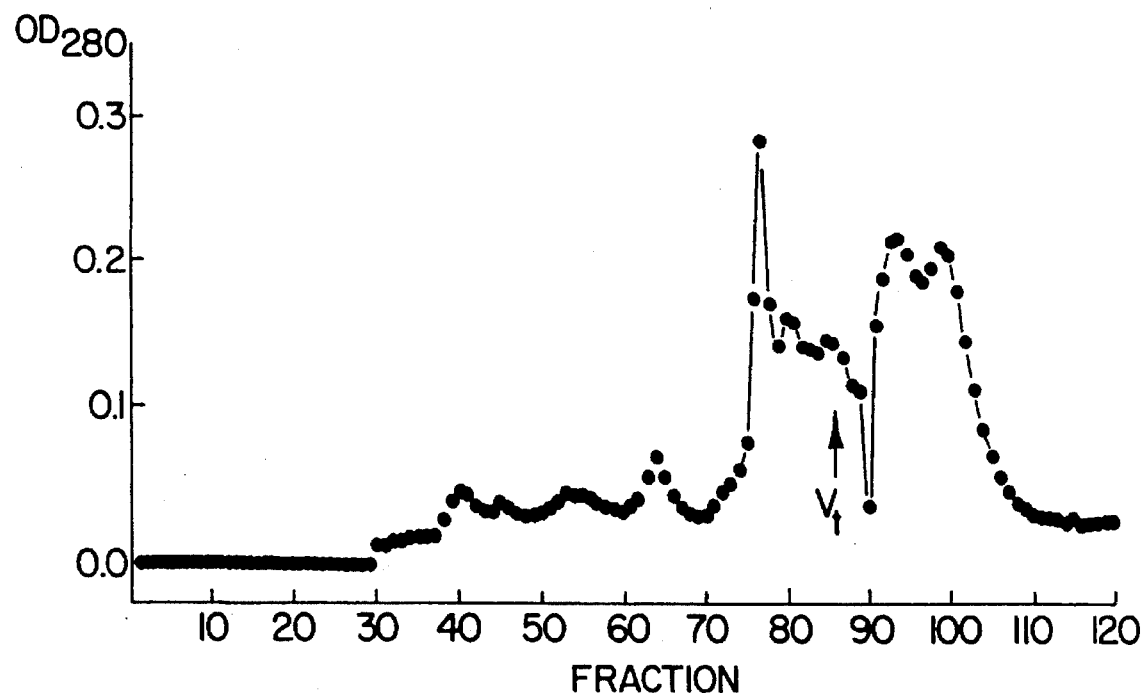
FIG. 1 shows the elution pattern of a concentrate of the ultrafiltrate of porcine leukocytes applied to a Biogel P10 column.

The peptides of the invention are described by the formula:

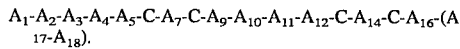

$A_1\text{-}A_2\text{-}A_3\text{-}A_4\text{-}A_5\text{-}C\text{-}A_7\text{-}C\text{-}A_9\text{-}A_{10}\text{-}A_{11}\text{-}A_{12}\text{-}C\text{-}A_{14}\text{-}C\text{-}A_{16}\text{-}(A_{17}\text{-}A_{18})$.

The designation $A_n$ in each case represents an amino acid at the specified position in the peptide. As $A_{17}$ and $A_{18}$ may or may not be present, the peptides of the invention contain either 16, 17 or 18 amino acids. The positions of the cysteine residues, as shown in Formula 1, are invariant in the peptides of the invention.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

The peptides of the invention may be in straight chain or cyclic form. The straight chain forms are convertible to the cyclic forms. The cyclic forms are the result of the formation of cystine linkages among the four invariant cysteine residues. Cyclic forms of the invention include all possible permutations of cystine bond formation; if the cysteines are numbered in order of their occurrence starting at the N-terminus as $C_1$, $C_2$, $C_3$ and $C_4$, these permutations include:

$C_1\text{–}C_2$, $C_3\text{–}C_4$;

$C_1\text{–}C_3$, $C_2\text{–}C_4$; and $C_1\text{–}C_4$, $C_2\text{–}C_3$.

The amino acids denoted by $A_n$ may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The amino acid notations used herein are conventional and are as follows:

| Amino Acid | One—Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

Acidic: Aspartic acid and Glutamic acid;

Basic:
  Noncyclic: Arginine, Lysine;
  Cyclic: Histidine;

Small: Glycine, Serine, Alanine, Threonine;

Polar/large: Asparagine, Glutamine;

Hydrophobic: Tyrosine, Valine, Isoleucine, Leucine, Methionine, Phenylalanine, Tryptophan.

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure is critical in the compounds of the present invention.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,

Sar, beta-Ala, 2,3-diaP and Aib are "Small";

t-BuA, t-BuG, N-MeIle, Nle, Mvl, Cha, Phg, Nal, Thi and Tic are hydrophobic;

Orn and Har are basic;

Cit, Acetyl Lys, and MSO are neutral/polar.

The various omega-amino acids are classified according to size as Small (beta-Ala, i.e., 3-aminopropionic, 4-aminobutyric) or large and hydrophobic (all others).

Other amino acid substitutions of those encoded in the gene can also be includedin peptide compounds within the scope of the invention and can be classified within this general scheme according to their structure.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—).

The compounds of Formula 1 are defined as follows:

$A_1$, $A_9$, $A_{10}$ and $A_{11}$ are basic amino acids;

$A_2$ and $A_3$ are small amino acids;

$A_5$, $A_7$, $A_{12}$, $A_{14}$ and $A_{16}$ are hydrophobic amino acids;

$A_4$ is a basic or a small amino acid;

$A_{17}$ is either not present or is a small amino acid; and $A_{18}$ is not present if $A_{17}$ is not present or, if $A_{17}$ is present, $A_{18}$ may be not present or is a basic amino acid.

In preferred embodiments of the compounds of the invention, $A_1$, $A_9$, A10 and $A_{11}$ are selected from the group consisting of R, K and Har; more preferably, all of $A_1$, $A_9$, $A_{10}$ and $A_{11}$ are R.

In another class of preferred embodiments, $A_2$ and $A_3$ are selected from the group consisting of G, A, S and T; more preferably, $A_1$ and $A_2$ are G.

In another set of preferred embodiments, $A_4$ is selected from the group consisting of R, K, Har, G, A, S and T; more preferably, $A_4$ is R or G.

In another set of preferred embodiments, $A_5$, $A_{14}$ and $A_{16}$ are selected independently from the group consisting of I, V and L and Nle; preferably I, V and L.

In another set of preferred embodiments, $A_7$ and $A_{12}$ are selected from the group consisting of W, Y and F; preferably $A_7$ is Y and $A_{12}$ is F.

$A_{17}$, when present, is preferably G, A, S or T, most preferably G;

$A_{18}$, when present, is preferably R, K or Har, most preferably R.

In an alternative embodiment, the peptides of the invention are defined as described by Formula 1, but wherein the definitions of $A_n$ in each case are determined by the isolatability of the peptide from animal leukocytes by the invention method. The invention method comprises the steps of providing an ultrafiltrate of a lysate of animal leukocytes and isolating peptides of 16–18 amino acids. These peptides can further be defined by the ability of DNA encoding them to hybridize under stringent conditions to DNA encoding the peptides exemplified as PG-1, PG-2, and PG-3 herein.

Particularly preferred compounds of the invention are:

PG-1: R—G—G—R—L—C—Y—C—R—R—R—F—C—V—C—V—G—R
(SEQ ID No: 1)
PG-2: R—G—G—R—L—C—Y—C—R—R—R—F—C—I—C—V
(SEQ ID No: 2)
PG-3: R—G—G—G—L—C—Y—C—R—R—R—F—C—V—C—V—G—R
R—G—G—R—L—C—Y—C—R—R—R—F—C—V—C—V
K—G—G—R—L—C—Y—C—R—R—R—F—C—V—C—V
R—G—G—Har—L—C—Y—C—R—R—R—F—C—V—C—V
R—G—G—Har—L—C—Y—C—Har—R—R—F—C—V—C—V—G—R
R—G—G—R—L—C—Y—C—R—K—K—W—C—V—C—V—G—R
R—G—G—R—L—C—Y—C—R—Har—R—Y—C—V—C—V—G—R
R—G—S—G—L—C—Y—C—R—R—K—W—C—V—C—V—G—R
R—A—T—R—I—C—F—C—R—R—R—F—C—V—C—V—G—R
R—G—G—K—V—C—Y—C—R—Har—R—F—C—V—C—V—G—R
R—A—T—R—I—C—F—C—R†—R—R—F—C—V—C—V—G—R†
R—G—G—K—V—C—Y—C—R—Har†—R—F—C—V—C—V—G—R

Preparation of the Invention Compounds

The invention compounds, often designated herein "protegrins" are essentially peptide backbones which may be modified at the N- or C-terminus and also contain, when in active form, two cystine disulfide linkages. The peptides may first be synthesized in noncyclized form and these intermediates converted to the cyclic peptides by standard methods of cystine bond formation. As applied to the protegrins herein, "cyclic forms" refers to those forms which contain cyclic portions by virtue of the formation of disulfide linkages between cysteine residues in the peptide.

Standard methods of synthesis of peptides the size of protegrins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in, the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The Carboxy terminus may also be esterified using alcohols of 5he formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

Formation of disulfide linkages is conducted in the presence of mild oxidizing agents. Chemical oxidizing agents may be used, or the compounds may simply be exposed to the oxygen of the air to effect these linkages.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host. Alternatively, although less convenient, the DNA can be obtained, at least initially, by screening a cDNA library prepared from porcine leukocytes using probes or PCR primers based on the sequences of the protegrins described herein. This results in recovery of the naturally occurring sequence encoding the protegrins of the invention. Obtention of this native sequence is significant for purposes other than the synthesis of the protegrins per se; the availability of the naturally occurring sequences provides a useful probe to obtain corresponding DNA encoding protegrins of other species. Thus, cDNA libraries, for example, of leukocytes derived from other animals can be screened using the native DNA, preferably under conditions of high stringency. High stringency is as defined by Maniatis, et al. *Molecular Cloning: a Laboratory Manual* 2nd Ed, Cold Spring Harbor Laboratory Press (1989), the relevant portions of which are incorporated herein by reference. This procedure also permits recovery of allelic variants of these peptides from the same species.

Alternatively, the protegrins can be prepared by isolation from leukocytes of a desired species using techniques similar to those disclosed herein for the isolation of porcine protegrins. In general, these techniques involve preparing a lysate of a leukocyte preparation, ultrafiltering the supernatant of the clarified lysate and recovering the ultrafiltrate. The ultrafiltrate is then subjected to chromatographic separation. The location of fragments having antimicrobial and antiviral activity corresponding to protegrins can be assessed using criteria of molecular weight and assaying the fractions for the desired activities as described herein.

Isolated and recombinantly produced forms of the protegrins may require subsequent derivatization to modify the N- and/or C-terminus and to effect the formation of cystine bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The protegrins of the invention can be produced in a form that will result in their secretion from the host cell by fusing to the DNA encoding the protegrin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the protegrins of the invention can be produced in a variety of modalities including chemical synthesis, recombinant production, isolation from natural sources, or some combination of these techniques.

Those members of the protegrin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the protegrins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The protegrins of the invention in immunogenic form are then injected into a suitable mammalian host and antibody titers in the serum are monitored. Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

The antibodies of the invention are, of course, useful in immunoassays for determining the amount or presence of the protegrins. Such assays are essential in quality controlled production of compositions containing the protegrins of the invention. In addition, the antibodies can be used to assess the efficacy of recombinant production of the protegrins, as well as screening expression libraries for the presence of protegrin encoding genes.

Compositions Containing the Protegrins and Methods of Use

The protegrins of the invention are effective in inactivating a wide range of microbial and viral targets, including Gram positive and Gram negative bacteria, yeast, and certain strains of virus. Accordingly, they can be used in disinfectant compositions and as preservatives for materials such as foodstuffs, cosmetics, medicaments, or other materials containing nutrients for organisms. For use in such contexts, the protegrins are supplied either as a single protegrin, in admixture with several other protegrins, or in admixture with additional antimicrobial agents. In general, as these are preservatives in this context, they are usually present in relatively low amounts, of less than 5%, by weight of the total composition, more preferably less than 1%, still more preferably less than 0.1%.

For use as antimicrobials or antivirals for treatment of animal subjects, the protegrins of the invention can be formulated as pharmaceutical or veterinary compositions. Depending on the subject to be treated, the mode of administration, and the type of treatment desired—e.g., prevention, prophylaxis, therapy; the protegrins are formulated in ways consonant with these parameters. A summary of such techniques is found in Remington's *Pharmaceutical Sciences*, latest edition, Mack Publishing Co., Easton, Pa.

The protegrins of the invention can be administered singly or as mixtures of several protegrins or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The protegrins can be administered also in liposomal compositions or as microemulsions.

If administration is to be oral, the protegrins of the invention must be protected from degradation in the stomach using a suitable enteric coating. This may be avoided to some extent by utilizing amino acids in the D-configuration, thus providing resistance to proteases. However, the peptide is still susceptible to hydrolysis due to the acidic conditions of the stomach; thus, some degree of enteric coating may still be required.

The protegrins of the invention may also be applied to plants or to their environment to prevent viral- and microbial-induced diseases in these plants. Suitable compositions for this use will typically contain a diluent as well as a spreading agent or other ancillary agreements beneficial to the plant or to the environment.

Thus, the protegrins of the invention may be used in any context wherein an antimicrobial and/or antiviral action is required. This use may be an entirely in vitro use, or the peptides may be administered to organisms.

In addition, the antimicrobial or antiviral activity may be generated in situ by administering an expression system suitable for the production of the protegrins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

A particularly useful property of the protegrins is their activity in the presence of serum. Unlike defensins, protegrins are capable of exerting their antimicrobial effects in the presence of serum.

The following examples are intended to illustrate but not to limit the invention.

EXAMPLE 1

Isolation of PG-1, PG-2 and PG-3

Fresh porcine blood was collected into 15-liter vessels containing 5% EDTA in normal saline, pH 7.4 as an anticoagulant (33 ml/liter blood). The blood cells were allowed to sediment for 90 minutes at room temperature and the leukocyte-rich supernatant was removed and centrifuged at 200×g for 5.7 minutes. The pellets were pooled and suspended in 0.84% ammonium chloride to lyse erythrocytes and the resulting leukocytes (70–75% PMN, 5–10% eosinophils, 15–25% lymphocytes and monocytes) were washed in normal saline, resuspended in ice-cold 10% acetic acid at $10^8$/ml, homogenized and stirred overnight at 4° C. The preparation was centrifuged at 25,000×g for 3 hours at 4° C. and the supernatant was lyophilized and weighed.

950 mg (dry weight) of lyophilized extract, which contained 520 mg protein by BCA analysis, was stirred overnight at 4° C. in 100 ml of 10% acetic acid and then centrifuged at 25,000×g for 2 hours. The supernate was removed and passed by pressure through a 50 ml stirred ultracentrifugation cell (Amicon, Danvers Mass.) that contained a YM-5 filter. The ultrafiltrate (24.5 mg protein by BCA) was concentrated to 3 ml by vacuum centrifugation (SpeedVac Concentrator, Savant Instruments, Hicksville, N.Y.), applied to a 2.5×117 cm BioGel P10 column (Bio-Rad, Hercules, Calif.) and eluted at 4° C. with 5% acetic acid.

Fractions containing 6.6 ml were obtained. Fractions were assayed by absorption at 280 nm and the elution pattern is shown in FIG. 1.

Figure 2:
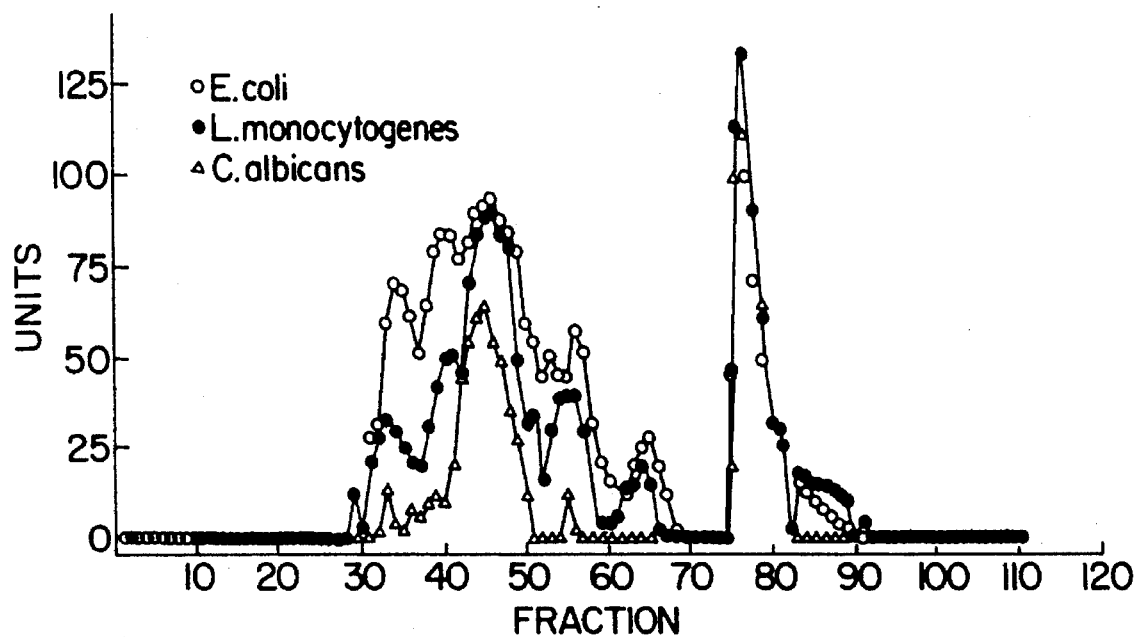
FIG. 2 shows the antibacterial activity of the P10 fractions obtained from elution of the column described in FIG. 1.

Aliquots (66 μl) of each fraction were dried by vacuum centrifugation and resuspended in 6.6 μl of 0.01% acetic acid. Five μl samples of this concentrate were tested for antimicrobial activity against *E. coli* ML-35, *L. monocytogenes*, strain EGD and *C. albicans*, strain 820, using radiodiffusion and gel overlay techniques as described by Lehrer, R. I. et al. *J Immuno Meth* (1991) 137:167–173. Briefly, the underlay agars used for all organisms had a final pH of 6.5 and contained 9 mM sodium phosphate/1 mM sodium citrate buffer, 1% w/v agarose and 0.30 mg/ml tryptocase soy broth powder (BBL Cockeysville, Md.). The units of activity in the radial diffusion assay were measured as described; 10 units correspond to a 1 mm diameter clear zone around the sample well. Activities obtained for the various fractions are shown in FIG. 2. Activity was found in a large number of fractions.

The active fractions were further examined by acid-urea PAGE and SDS PAGE. Results of these analyses showed that active antimicrobial peptides of the appropriate molecular weight were present and concentrated in fractions 76–78.

Figure 3:
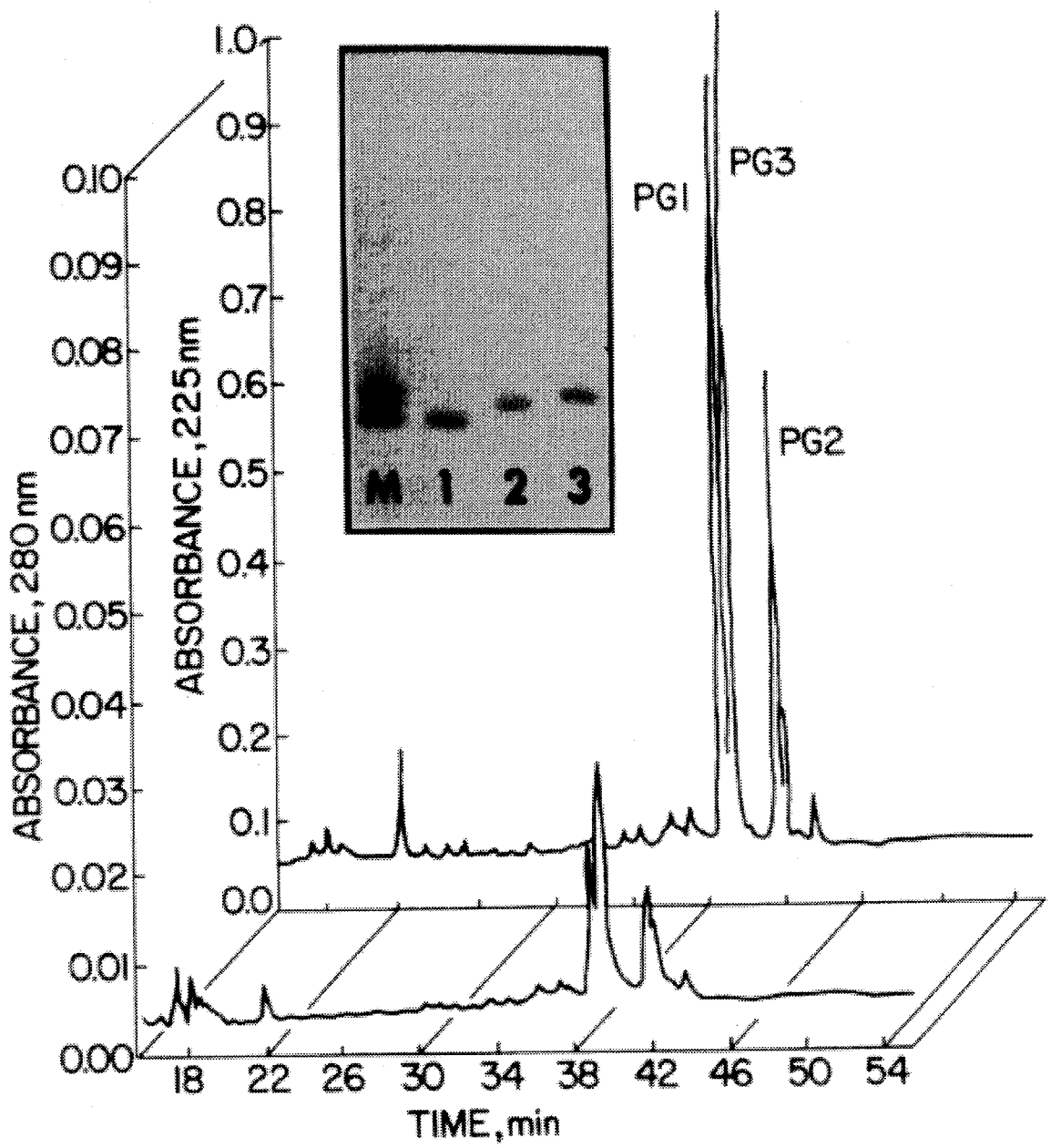
FIG. 3 shows an elution pattern obtained when fractions 76–78 from the Biogel P10 column of FIG. 1 is applied to HPLC.

Fractions 76–78 from the Biogel P10 column were then pooled and chromatographed on a 1×25 cm Vydac 218 TP1010 column with a gradient (buffer A is 0.1% TFA; buffer B is 0.1% TFA in acetonitrile) the increase in acetonitrile concentration was 1% per minute. The results, assessed in terms of absorbance at 280 nm and at 225 nm are shown in FIG. 3. The peaks corresponding the three peptides illustrated herein are labeled in the figure. The figure also contains an inset which shows the results of an acid-urea PAGE gel stained with Comassie Blue that contains a starting mixture composed of the pooled fractions and the individual PG species. These are labeled M, 1, 2 and 3 on the inset. The results clearly show the presence of three distinct proteins.

The isolated proteins were subjected to amino acid analysis using three independent methods, and to Edman degradation, chymotrypsin digestion, and fast atom bombardment mass spectrometric analysis. The peptides, named "protegrins", are shown to have the amino acid sequences as follows:

| | |
|---|---|
| PG-1: RGGRLCYCRRRFCVCVGR | (SEQ ID NO:1) |
| PG-2: RGGRLCYCRRRFCICV | (SEQ ID NO:2) |
| PG-3: RGGGLCYCRRRFCVCVGR | (SEQ ID NO:3) |

The antimicrobial proteins above are present in much lower concentrations in initial extracts than are the rabbit defensins in corresponding crude extracts where the defensins constitute more than 15% of the total protein in rabbit granulocytes. Using the AU-PAGE analytical method on the various stages of purification, the peptides are only faintly visible in the crude extracts, whereas corresponding crude extracts of rabbit granulocytes clearly show the presence of the defensins. The peptides of the invention become clearly evident only after the ultrafiltration step.

Because the protegrins whose structures are set forth above show sequence homology to the decapeptide region corresponding to residues 1–10 of rabbit defensin NP-3a in the decapeptide region at positions 4–13 of PG-3, the protegrins, and in particular PG-3, may share the property of defensin NP-3a in being capable of competitively antagonizing ACTH-mediated steroid synthesis by adrenocytes. This property, called "corticostasis", may influence the effectiveness of the protegrins as antiinfectious agents when employed in vivo.

EXAMPLE 2

Antimicrobial Activity

Figure 4A:
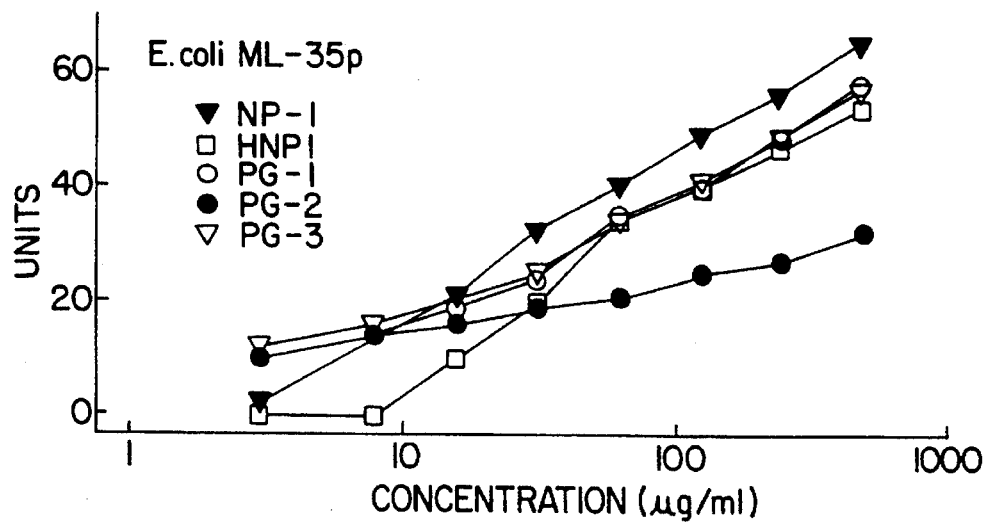
FIGS. 4a–4c show the antimicrobial activity of the purified porcine protegrins of the invention.
Figure 4B:
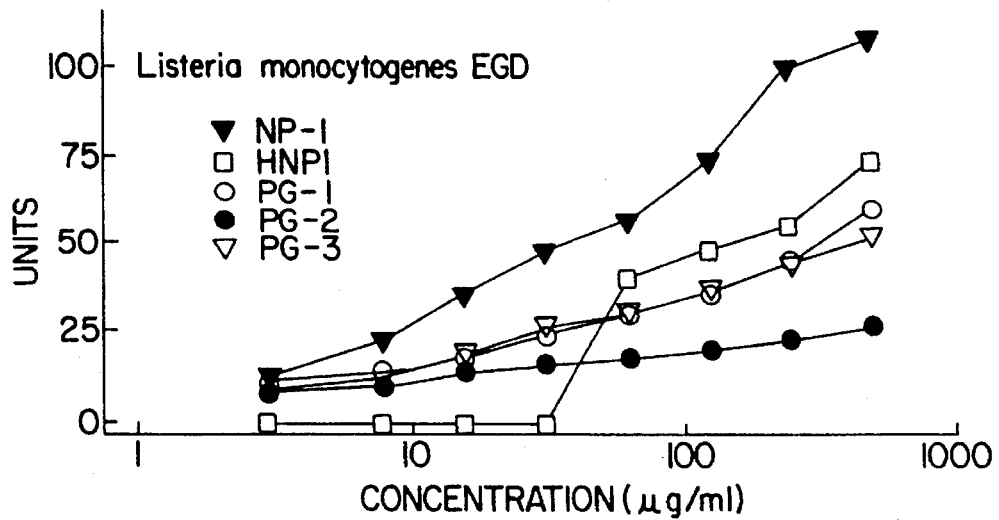
Figure 4C:
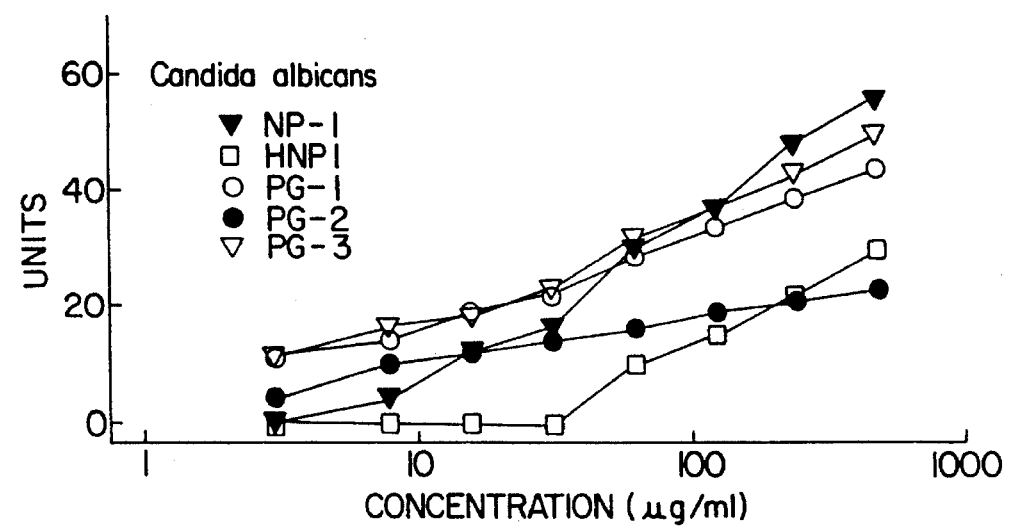

The radial diffusion assay in agarose gels described in Example 1 was also used to test the activity of the purified protegrins. FIGS. 4a, 4b and 4c show the results against three test organisms in units described as above. The rabbit defensin (NP-1) and the human defensin (HNP-1) were used as controls.

FIG. 4a shows that PG-1 and PG-3 are more effective against *E. coli* ML-35P than HNP-1 and only slightly less effective than NP-1. PG-1 and PH-3 were also effective against *Listeria monocytogenes*, strain EGD as shown in FIG. 4b. In FIG. 4c, PG-1 and PG-3 were also shown effective against *Candida albicans*. In general, these peptides are approximately as effective as rabbit defensin NP-1 on a weight basis and are more effective than HNP-1. In all cases, PG-2 was also effective against the three organisms tested but was not as active as the other two peptides.

EXAMPLE 3

Retention of Activity Under Certain Conditions

Figures 1, 5A:
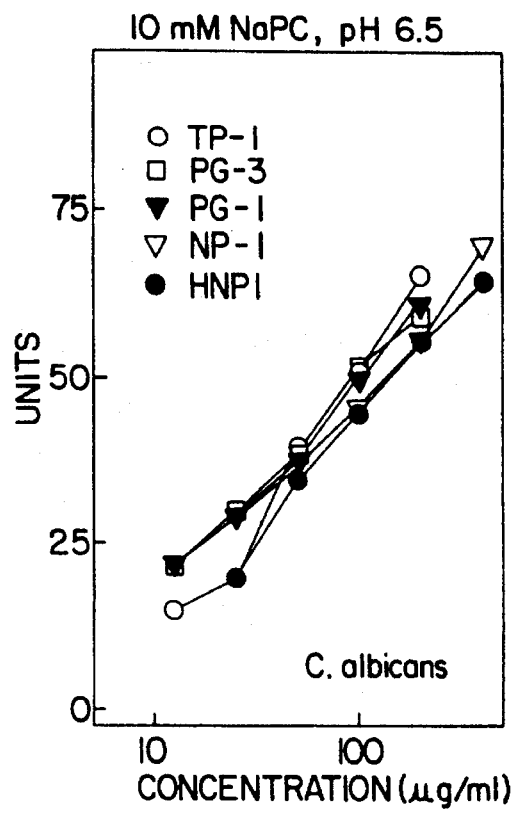
FIGS. 5a–5c show retention of activity under various conditions.
Figures 2, 5A:
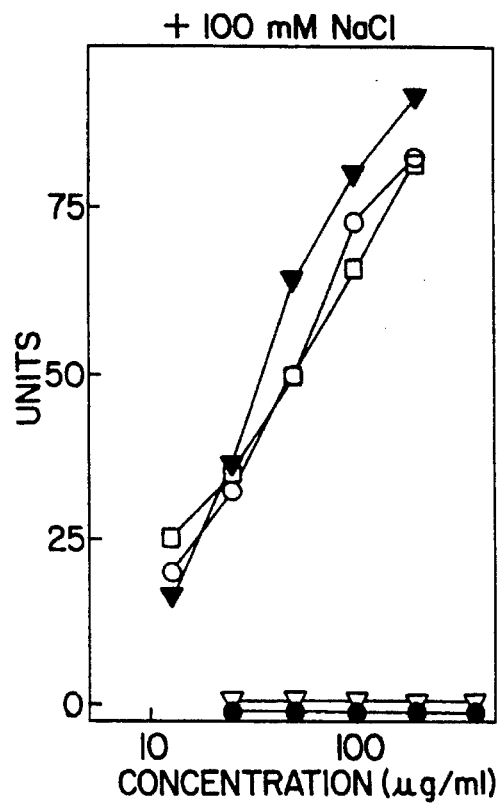
Figures 1, 5B:
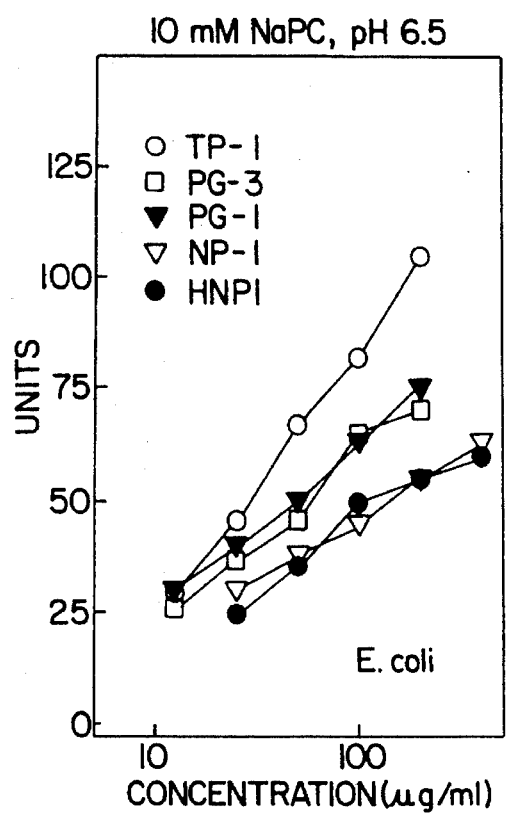
Figures 2, 5B:
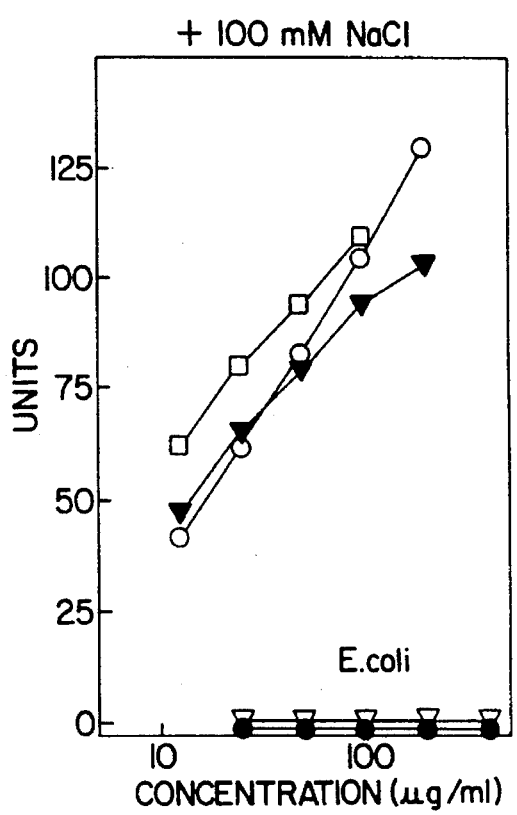
Figures 1, 5C:
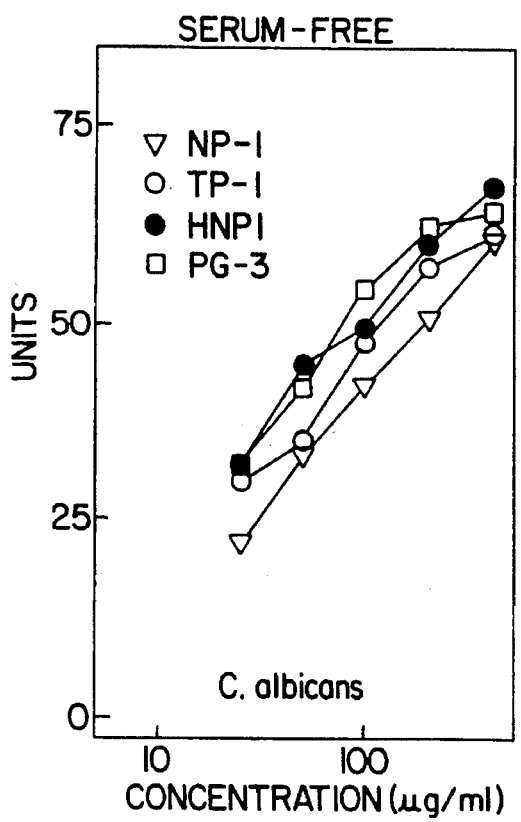
Figures 2, 5C:
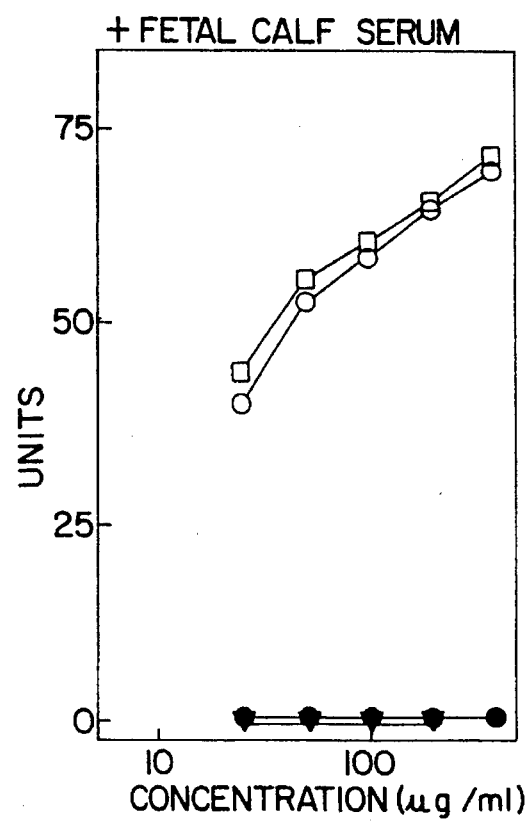

The antimicrobial activity of the invention compounds was tested as set forth above, but under conditions of 100 µM Nacl and in the presence of 90% fetal calf serum. FIGS. 5a and 5b show that PG-1 and PG-3 retain their activity with respect to *C. albicans* and *E. coli* respectively, even in the presence of 100 µM Nacl. Neither NP-1 nor HNP-1 have this property. FIG. 5c shows that although NP-1 and NHP-2 lose their ability to inactivate *C. albicans* in 90% feital calf serum, inactivation by PG-3 is retained.

Accordingly, the protegrins of the invention retain their antimicrobial properties under useful conditions.

We claim:

1. A purified and isolated compound having antimicrobial activity against *E. coli*, *L. monocytogenes* or *Candida albicans*, said compound being of the formula $A_1$-$A_2$-$A_3$-$A_4$-$A_5$-C-$A_7$-C-$A_9$-$A_{10}$-$A_{11}$-$A_{12}$-C-$A_{14}$-C-$A_{16}$ (SEQ ID NO:4)

and the N-terminal acylated, C-terminal amidated or esterified and the cystine-bridged forms thereof wherein $A_1$, $A_9$, $A_{10}$ and $A_{11}$ are basic amino acids;

$A_2$ and $A_3$ are small amino acids;

$A_5$, $A_7$, $A_{12}$, $A_{14}$ and $A_{16}$ are hydrophobic amino acids; and $A_4$ is a basic or a small amino acid;

$A_{17}$ is not present or, if present, is a small amino acid;

$A_{18}$ is not present or, if present, is a basic amino acid.

2. The compound of claim 1 which contains two cystine bridges.

3. The compound of claim 1 wherein the C-terminal carboxyl is of the formula selected from the group consisting of COOH or the salts thereof; COOR, $CONH_2$, CONHR, and $CONR_2$ wherein each R is independently hydrocarbyl(1–6C).

4. The compound of claim 1 wherein the amino group at the N-terminus is of the formula $NH_2$ or NHCOR wherein R is hydrocarbyl(1–6C).

5. The compound of claim 1 wherein each of $A_1$, $A_9$, $A_{10}$ and $A_{11}$ is independently selected from the group consisting of R, K and Har.

6. The compound of claim 1 wherein each of $A_1$, $A_9$, $A_{10}$ and $A_{11}$ is R.

7. The compound of claim 1 wherein each of $A_2$ and $A_3$ is selected independently from the group consisting of G, A, S and T.

8. The compound of claim 1 wherein each of $A_2$ and $A_3$ is G.

9. The compound of claim 1 wherein $A_4$ is R or G.

10. The compound of claim 1 wherein each of $A_5$, $A_{14}$ and $A_{16}$ is independently selected from the group consisting of I, V and L.

11. The compound of claim 10 wherein $A_5$ is L and $A_{16}$ is V.

12. The compound of claim 1 wherein each of $A_7$ and $A_{12}$ is independently selected from the group consisting of W, Y and F.

13. The compound of claim 12 wherein $A_7$ is Y or $A_{12}$ is F.

14. A purified and isolated compound of a formula which is selected from the group consisting of

| PG-1: RGGRLCYCRRRFCVCVGR | (SEQ ID NO:1) |
| PG-2: RGGRLCYCRRRFCICV | (SEQ ID NO:2) |
| PG-3: RGGGLCYCRRRFCVCVGR | (SEQ ID NO:3). |

15. The compound of claim 1 wherein each of $A_1$, $A_9$, $A_{10}$ and $A_{11}$ is independently selected from the group consisting of R, K and Har;

each of $A_2$ and $A_3$ is independently selected from the group consisting of G, A, S and T;

$A_4$ is R or G; and each of $A_5$, $A_{14}$ and $A_{16}$ is independently selected from the group consisting of I, V and L; and each of $A_7$ and $A_{12}$ is independently selected from the group consisting of W, Y and F.

16. The compound of claim 15 wherein each of $A_1$, $A_9$, $A_{10}$ and $A_{11}$ is R;

each of $A_2$ and $A_3$ is G;

$A_4$ is R or G; and $A_7$ is Y or $A_{12}$ is F.

17. A pharmaceutical composition for antimicrobial or antiviral use which comprises the compound of claim 1 in admixture with at least one pharmaceutically acceptable excipient.

18. A composition for application to plants or plant environments for conferring resistance to microbial or viral infection in plants which comprises the compound of claim 1 in admixture with at least one environmentally acceptable diluent.

* * * * *

UNITED STATES PATENT AND TRADEMARK OFFICE
CERTIFICATE OF CORRECTION

PATENT NO. : 5,464,823

DATED : November 7, 1995

INVENTOR(S) : Robert I. LEHRER et al.

It is certified that error appears in the above-identified patent and that said Letters Patent is hereby corrected as shown below:

Column 19, line 31, should read:

$A_1$-$A_2$-$A_3$-$A_4$-$A_5$-C-$A_7$-C-$A_9$-$A_{10}$-$A_{11}$-$A_{12}$-C-$A_{14}$-C-$A_{16}$-($A_{17}$-$A_{18}$) (1) (SEQ ID NO:4)

Signed and Sealed this

Sixteenth Day of April, 1996

Attest:

BRUCE LEHMAN

*Attesting Officer*     *Commissioner of Patents and Trademarks*